(12) United States Patent
Falck-Pedersen et al.

(10) Patent No.: US 6,525,029 B1
(45) Date of Patent: Feb. 25, 2003

(54) METHOD OF INHIBITING AND IMMUNE RESPONSE TO A RECOMBINANT VECTOR

(75) Inventors: Erik S. Falck-Pedersen, Dobbs Ferry, NY (US); Keith Elkon, Larchmont, NY (US)

(73) Assignees: Cornell Research Foundation, Inc., Ithaca, NY (US); Hospital for Special Surgery, New York, NY (US)

( * ) Notice: Subject to any disclaimer, the term of this patent is extended or adjusted under 35 U.S.C. 154(b) by 0 days.

(21) Appl. No.: 09/182,567

(22) Filed: Oct. 29, 1998

Related U.S. Application Data

(60) Provisional application No. 60/063,580, filed on Oct. 30, 1997.

(51) Int. Cl.⁷ ............... A61K 48/00; A61K 38/00; C12N 15/63; C12N 15/85; C07K 14/00
(52) U.S. Cl. .............. 514/44; 435/320.1; 435/325; 514/2; 530/350
(58) Field of Search ............ 514/44, 2; 435/325, 435/320.1; 530/350

(56) References Cited

U.S. PATENT DOCUMENTS

| | | | |
|---|---|---|---|
| 4,518,584 A | 5/1985 | Mark et al. | 424/85.2 |
| 4,737,462 A | 4/1988 | Mark et al. | 435/252.33 |
| 5,447,851 A | 9/1995 | Beutler et al. | 435/69.7 |
| 5,623,056 A | 4/1997 | Tyocinski et al. | 530/403 |

FOREIGN PATENT DOCUMENTS

| | | |
|---|---|---|
| DE | 4447848 | 10/1995 |
| EP | 595659 | 5/1994 |
| EP | 0614981 A1 * | 9/1994 |
| EP | 614981 | 9/1994 |
| WO | WO 94/28938 | 12/1994 |
| WO | WO 96/10088 | 4/1996 |
| WO | WO 96/12030 | 4/1996 |
| WO | WO 96/25177 | 8/1996 |
| WO | WO 96/39514 | 12/1996 |

OTHER PUBLICATIONS

Kayagaki et al. (1997) Proc. Natl. Acad. Sci., vol. 94, 3914–3919, 1997.*
Scheider et al. (1997) J. Biol. Chem., vol. 272 (30), 18827–18833, 1997.*
Le et al. (1997) Arth. & Rheum., vol. 40 (9), 1662–1669, 1997.*
Adams et al., *J. Infectious Diseases*, 171, 400–405 (1995).
Bauer et al., *Gene*, 37, 73–81 (1985).
Berkner, *BioTechniques*, 6, 616–629 (1988).
Beyaert et al., *FEBS Lett.*, 340, 9–16 (1994).
Biron, *Current Opinion in Immunology*, 6, 530–538 (1994).
Bruder et al, *J. Virol.*, 71(1), 398–404 (1997).
Brunner et al., *Nature*, 373, 441–443 (1995).
Bullard et al., *J. Immunology*, 159, 2058–2067 (1997).
Chu et al., *J. Exp. Med.*, 181, 393–398 (1995).
Cleveland et al., *Cell*, 81, 479–482 (1995).
Cotten et al., *PNAS USA*, 89, 6094–6098 (1992).
Craik, *Biotechniques*, 3(1), 12–19 (Jan. 1985).
Crispe, *Immunity*, 1, 347–349 (1994).
Curiel et al., *PNAS USA*, 88, 8850–8854 (1991).
Curiel et al., *Human Gene Therapy*,3, 147–154 (1992).
Dai et al., *PNAS USA*, 92, 1401–1405 (1995).
Devereux et al., *Nucleic Acids Res.*, 12, 387–395 (1984).
Dighe et al., *Immunity*, 1, 447–456 (1994).
Drappa et al., *PNAS USA*, 90, 10340–10344 (1993).
Fukada et al., *Immunity*, 5, 449–460 (1996).
Gall et al., *J. Virol.*, 70, 2116–2123 (1996).
Ginsberg et al., *PNAS USA*, 86, 3823–3827 (1989).
Ginsberg et al., *PNAS USA*, 87, 6191–6195 (1990).
Ginsberg et al., *PNAS USA*, 88, 1651–1655 (1991).
Guerette et al., *Transplantation*, 62, 962–967 (1996).
Guidotti et al., *PNAS USA*, 93, 4589–4594 (1996).
Guidotti et al., *Immunity*, 4, 25–36 (1996).
Hanabuchi et al., *PNAS USA*, 91, 4930–4934 (1994).
Heller et al., *Cell*, 73, 216 (1993).
Henkart, *Immunity*, 1, 343–346 (1994).
Horvath et al., *J. Virol.*, 70, 647–650 (1996).
Howard et al., *PNAS USA*, 90, 2335–2339 (1993).
Ilan et al., *PNAS USA*, 94, 2587–2592 (1997).
Itoh et al., *Cell*, 66, 233–243 (1991).
Jaffe et al., *Clin. Res.*, 39(2), 302A (1991).
Joose et al., *Human Gene Therapy*, 7, 1555–1566 (1996).
Ju et al., *Nature*, 373, 444–448 (1995).
Kägi et al., *Nature*, 369, 31–37 (1994).
Kägi et al., *Eur. J. Immunol.*, 25, 3256–3262 (1995).
Kass–Eisler et al., *PNAS USA*, 90, 11498–11502 (1993).
Kass–Eisler et al., *Gene Therapy*, 1, 395–402 (1994).
Kass–Eisler et al., *Gene Therapy*, 3, 154–162 (1996).
Kay et al., *Nat. Genet.*, 11, 191–197 (1995).
Kay et al., *PNAS USA*, 94, 4686–4691 (1997).
Kjellen et al., *J. Gen. Virol.*, 2, 177–185 (1968).
Kojima et al., *Immunity*, 1, 357–364 (1994).
Kolls et al., *PNAS USA*, 91, 215–219 (1994).

(List continued on next page.)

Primary Examiner—A.M. S. Beckerleg
(74) Attorney, Agent, or Firm—Leydig, Voit & Mayer, Ltd.

(57) ABSTRACT

The present invention provides, among other things, a method of inhibiting an immune response to a recombinant vector, such as a viral vector, specifically an adenoviral vector. The method comprises contacting a cell with (i) a recombinant vector, preferably a viral vector, most preferably an adenoviral vector, comprising a transgene and (ii) a means of inhibiting an immune response to the recombinant vector selected from the group consisting of a TNF receptor fusion protein, a Fas receptor fusion protein, an IFN receptor fusion protein, a gene encoding a TNF receptor fusion protein, a gene encoding a Fas receptor fusion protein, and a gene encoding an IFN receptor fusion protein, whereupon an immune response to the recombinant vector is inhibited. In this regard, the present invention also provides a recombinant vector and a composition for use in the method.

6 Claims, No Drawings

OTHER PUBLICATIONS

Kolls et al., *Human Gene Therapy*, 7, 489–497 (1996).
Lau et al., *Science*, 273 109–112 (1996).
Le et al., *Arthritis & Reumatism*, 40(9), 1662–1669 (1997).
Lei et al., *Human Gene Therapy*, 7, 2273–2279 (1996).
Li et al., *Human Gene Therapy*, 4, 403–409 (1993).
Loetscher et al., *J. Biol. Chem.*, 266 (27), 18324–18329 (1991).
Lowin et al., *Nature*, 370, 650–652 (1994).
Luckow et al., *Bio/Technology*, 6, 47 (1988).
Mack et al., *Human Gene Therapy*, 8, 99–109 (1997).
Marino et al., *PNAS USA*, 94, 8093–8098 (1997).
Martz et al., *Immunology Today*, 10 (3), 79–87 (1989).
Mastrangeli te al., *Human Gene Therapy*, 7, 79–87 (1996).
Matsuzawa et al., *J. Exp. Med.*, 171, 519–531 (1990).
McCoy et al., *Human Gene Therapy*, 6, 1553–1560 (1995).
Nagata et al., *Immunology Today*, 16 (1), 39–43 (1995).
Ogasawara et al., *Nature*, 364, 806–809 (1993).
Onel et al., *Eur. J. Immunol.*, 25, 2940–2947 (1995).
Orlinick et al., *J. Biol. Chem.*, 272, 32221–32229 (1997).
Pasparakis et al., *J. Exp. Med.*, 184(4), 1397–1411 (1996).
Peppel et al., *J. Exp. Med.*, 174, 1483–1489 (1991).
Rosenfeld et al., *Clin. Res.*, 39(2), 311A (1991).
Rosenfeld et al., *Science*, 252, 431–434 (1991).
Sharf et al., *J. Biol. Chem.*, 270, 13063–13069 (1995).
Smith et al., *Cell*, 76, 959–962 (1994).
Springer, *Nature*, 346, 425–434 (1990).
Stalder et al., *J. Immunol.*, 152, 1127–1133 (1994).
Suda et al., *Cell*, 75, 1169–1178 (1993).
Takahashi et al., *Cell*, 76, 969–976 (1994).
Takahashi et al., *International Immunology*, 6 (10), 1567–1574 (1994).
Tartaglia et al., *Cell*, 73, 213–216 (1993).
Tartaglia et al., *Cell*, 74, 845–853 (1993).
Tewari et al., *J. Biol. Chem.*, 270 (7), 3255–3260 (1995).
Thornton et al., *J. Immunol.*, 157, 5145–5154 (1996).
Trauth et al., *Science*, 245, 301–305 (1989).
Tripathy et al, *Nature Medicine*, 2(5), 545–550 (1996).
Vilquin et al., *Human Gene Therapy*, 6, 1391–1401 (1995).
Wagner et al., *PNAS USA*, 89, 6099–6103 (1992).
Walder et al., *Gene*, 42, 133 (1986).
Walsh et al., *PNAS USA*, 91, 10854–10858 (1994).
Watanabe–Fukunaga et al., *Nature*, 356, 314–317 (1992).
Watkins et al., *Immunotechnology (Amsterdam)*, 2(4), 307 (1996).
Wickelgren, *Science*, 273, 33 (1996).
Wilmott et al., *Human Gene Therapy*, 7, 301–318 (1996).
Wohlfart, *J. Virology*, 62(7), 2321–2328 (1988).
Wohlfart et al., *J. Virology*, 56(3), 896–903 (1985).
Worgall et al., *Human Gene Therapy*, 8, 37–44 (1997).
Yang et al., *PNAS USA*, 91, 4407–4411 (1994).
Yang et al., *J. Virol.*, 69(4), 2004–2015, (1995).
Yang et al., *J. Immunol.*, 155, 2564–2570 (1995).
Yang et al., *PNAS USA*, 92, 7257–7261 (1995).
Yang et al., *Gene Therapy*, 3, 137–144 (1996).
Yang et al., *Gene Therapy*, 3, 412–420 (1996).
Yang et al., *J. Virol.*, 70(9), 6370–6377 (1996).
Yang et al., *J. Virol.*, 70(10), 7209–7212 (1996).
Yang et al., *Science*, 273, 1862–1864 (1996).
Elkon et al., *Proc. Natl. Acad. Sci. USA*, 94, 9814–9819 (Sep. 1997).

* cited by examiner

METHOD OF INHIBITING AND IMMUNE RESPONSE TO A RECOMBINANT VECTOR

This application claims priority under 35 U.S.C. §119(e) to U.S. provisional patent application Ser. No. 60/063,580, which was filed on Oct. 30, 1997, now abandoned.

TECHNICAL FIELD OF THE INVENTION

The present invention relates to a method of inhibiting an immune response to a recombinant vector, as well as a vector and a composition for use in the method.

BACKGROUND OF THE INVENTION

A broad spectrum of eukaryotic viruses, including adenoviruses, adeno-associated viruses, Herpes viruses and retroviruses, has been used in gene therapy. Each type of vector has demonstrated a viral-dependent combination of advantages and disadvantages. Accordingly, careful consideration must be given to the advantages and disadvantages inherent to a particular type of vector when deciding which vector should be used in a particular application of gene therapy.

The advantages of adenoviruses with respect to gene therapy include ease of use, high titer production (i.e., up to about $10^{13}$ viral particles/ml), efficient gene transfer to nonreplicating, as well as replicating, cells (see, for example, review by Crystal, *Science*, 270, 404–410 (1995)), and a broad range of host- and cell-type specificity. Such advantages have resulted in a recombinant adenovirus being the vector of choice for a variety of gene transfer applications. Adenoviral vectors are especially preferred for somatic gene therapy of the lungs, given their normal tropism for the respiratory epithelium.

Other advantages that accompany the use of adenoviruses as vectors for gene therapy include: (1) the rare observance of recombination; (2) the absence of an ostensible correlation of any human malignancy with adenoviral infection, despite the common occurrence of infection; (3) the adenoviral genome (which is comprised of linear, double-stranded DNA) can be manipulated to carry up to about 7.5 kb of exogenous DNA, and longer DNA sequences can potentially be carried into a cell, for instance, by attachment to the adenoviral capsid (Curiel et al., *Human Gene Therapy*, 3, 147–154 (1992)); (4) an adenovirus is unlikely to interfere with normal cellular function since the vector controls expression of its encoded sequences in an epichromosomal manner; and (5) it already has been proven safe to use in humans, given that live adenovirus has been safely used as a human vaccine for many years.

Using adenoviral reporter gene constructs, it has been established that high levels of gene expression can be obtained in a variety of animal models. However, it also has been established that the high level of gene expression so obtained is transient, with reporter gene expression peaking within the first week after infection and becoming essentially undetectable about 80 days after infection. Recent studies have indicated that the limited persistence of gene expression in vivo is most likely due to an immune response of the host against virally infected cells. For example, gene expression can be maintained in immunologically privileged neuronal or retinal tissues for periods in excess of two months and in immunodeficient or immunologically naive rodents for periods in excess of six months.

Intravenous administration of adenovirus to mice results in the vast majority of adenovirus being localized to the liver (Worgall et al., *Human Gene Therapy*, 8, 37–44 (1997)). During the first 24–48 hrs of infection, 90% of vector DNA is eliminated, presumably through innate pathways of viral clearance mediated by Kupffer cells in the liver (Worgall et al. (1997), supra), well before maximal levels of transgene are expressed. In spite of the fact that the majority of virus is cleared within one to two days, over 95% of hepatocytes are transduced by the remaining small percentage of input adenoviral vectors (Li et al., *Human Gene Therapy*, 4, 403–409 (1993)) with maximum transgene expression occurring during the first week of post-infection. Transgene expression, however, rapidly declines to baseline levels in immune-competent animals within 2–3 weeks of infection due to immune activation.

Using a combination of mouse strains, which are defective in specific elements of the immune system, it has been shown that the immune response against cells infected with viral vectors involves both cellular and humoral components of the immune system. For example, immunodeficient mice, which lack mature T- and B-lymphocytes express adenovirus-mediated transgenes beyond four months (Kass-Eisler et al., *Gene Therapy*, 1, 395–402 (1994); Yang et al., *Immunity*, 1, 433–442 (1994a); Yang et al., *PNAS USA*, 91, 4407–4411 (1994b); Dai et al., *PNAS USA*, 92, 1401–1405 (1995); Kay et al., *Nat. Genet.*, 11, 191–197 (1995); and Yang et al., *J. Immunol.*, 155, 2564–2570 (1995)). Similarly, transfer of $CD8^+$ and $CD4^+$ cytotoxic T-cells from adenoviral vector-infected mice to infected RAG-2 mice, which lack mature B- and T-cell lymphocytes, resulted in clearance of the vector and transgene by apoptosis (Yang et al. (1994a), supra; and Yang et al. (1995), oupra), whereas immune depletion of $CD8^+$ or $CD4^+$ cells in immunocompetent mice results in persistent transgene expression (Yang et al. (1994a), supra; Kay et al.(1995), supra; Yang et al. (1995), supra; Kolls et al., *Hum. Gene Ther.*, 7, 489–497 (1996); and Guerette et al., *Transplantation*, 62, 962–967 (1996)). While pathways involving perforin and Fas are the major pathways responsible for T-cell cytotoxicity (Kojima et al., *Immunity*, 1, 357–364 (1994); Henkart, *Immunity*, 1, 343–346 (1994); Kagi et al., *Science*, 265, 528–530 (1994); and Kagi et al., *Eur. J. Immunol.*, 25, 3256–3262 (1995)), the perforin/granzyme pathway has been reported to mediate clearance of adenoviral gene transfer vectors by antigen-specific, cytotoxic T-cells (Yang et al., *PNAS USA*, 92, 7257–7261 (1995)).

In addition to limiting the persistence of gene expression from viral vectors, the immune response inhibits successful readministration of viral vectors, which limits the period of efficacy of gene therapy. For example, adenoviruses are classified into 47 different serotypes and a number of subgroups, namely A through G, based on a number of criteria, including antigenic crossreactivity. Following an initial administration of adenovirus, serotype-specific antibodies are generated against epitopes of the major viral capsid proteins, namely the penton, hexon and fiber. Given that such capsid proteins are the means by which the adenovirus attaches itself to a cell and subsequently infects the cell, such antibodies are then able to block or "neutralize" reinfection of a cell by the same serotype of adenovirus. This necessitates using a different serotype of adenovirus in order to administer one or more subsequent doses of exogenous DNA in the context of gene therapy.

The present invention seeks to address the problems presented by immune activation mediated by adenoviral gene transduction, as well as immune mediated apoptosis and anti-adenoviral neutralizing antibodies, which inhibit successful readministration of a viral vector, such as in the context of gene therapy. Accordingly, it is an object of the present invention to provide a method of inhibiting an immune response to a recombinant vector, as well as a vector and a composition for carrying out the method. These and other objects and advantages of the present invention, as well as additional inventive features, will be apparent from the following detailed description.

BRIEF SUMMARY OF THE INVENTION

The present invention provides, among other things, a method of inhibiting an immune response to a recombinant vector, such as a viral vector, specifically an adenoviral vector. The method comprises contacting a cell with (i) a recombinant vector, preferably a viral vector, most preferably an adenoviral vector, comprising a transgene and (ii) a means of inhibiting an immune response to the recombinant vector selected from the group consisting of a tumor necrosis factor (TNF) receptor fusion protein, a Fas receptor fusion protein, an interferon (IFN) receptor fusion protein, a dominant negative of an interferon consensus sequence binding protein (ICSBP), a gene encoding a TNF receptor fusion protein, a gene encoding a Fas receptor fusion protein, a gene encoding an IFN receptor fusion protein, and a gene encoding a dominant negative of an ICSBP, whereupon an immune response to the recombinant vector is inhibited. In this regard, the present invention also provides a vector and a composition for use in the method.

DETAILED DESCRIPTION OF THE INVENTION

The present invention is predicated, at least in part, on the understanding that the cellular components of the immune response are principally responsible for inhibiting persistent expression of a gene contained within an adenoviral vector and the humoral component of the immune response is principally responsible for inhibiting the successful readministration of an adenoviral vector of a given serotype in immune competent animals. This discovery is based on the observation that animals, which were defective for one or more genes involved in programmed cell death or "apoptosis," did not respond to the presence of an adenovirus and the subsequent readministration of an adenovirus of the same serotype. Specifically, Fas⁻ animals were compromised in their ability to respond immunologically to the continued presence of a given adenovirus and its subsequent readministration. TNF⁻ animals were immunologically severely impaired in their response to the continued presence of a given adenovirus and its subsequent readministration. These observations led to the surprising and unexpected discovery that inhibition of one or more cellular genes, which are involved in cell death and immune activation, such as the TNF, specifically TNF-α, Fas and/or IFN genes, enables persistent presence of a vector and persistent expression of a gene contained within the vector, particularly a viral vector, specifically an adenoviral vector, in a host cell and the successful readministration of the same vector or, in the case of an adenoviral vector, a vector of the same serotype, to the host cell, such as in the context of in vivo and in vitro (ex vivo) gene therapy.

In view of the above, the present invention provides a method of inhibiting an immune response to a recombinant vector, in particular a viral vector, such as an adenoviral vector, an adeno-associated viral vector, a herpes viral vector or a retroviral vector, preferably an an adenoviral vector, during the contact of a cell with a recombinant vector comprising a transgene and/or the expression of a transgene in a recombinant vector in a cell, such as in the context of in vivo and in vitro (ex vivo) gene therapy. By "inhibiting" is meant the direct or indirect, partial or complete, inhibition of an innate or acquired immune response, whether cellular (e.g., leukocyte recruitment) or humoral, to a recombinant vector, in particular a viral vector, specifically an adenoviral vector, especially when the vector is in the form of a recombinant viral particle as opposed to nonencapsidated nucleic acid, so as to enable persistent presence of the recombinant vector in the cell and concomitant persistent expression of a transgene contained within the vector. Such inhibition, however, desirably should not compromise the long-term immunity of a host, if a host is contacted with a recombinant vector comprising a transgene and a means of inhibiting an immune response to the recombinant vector in accordance with the present invention. By "immune response" is preferably meant an acquired immune response, such as a cellular or humoral immune response. "In vivo gene therapy" and "in vitro gene therapy" are intended to encompass all past, present and future variations and modifications of what is commonly known and referred to by those of ordinary skill in the art as "gene therapy," including ex vivo applications.

The method comprises contacting a cell with (i) a recombinant vector, preferably a viral vector, most preferably an adenoviral vector, comprising a transgene and (ii) a means of inhibiting an immune response to the recombinant vector, whereupon an immune response to the recombinant vector is inhibited. The method can be used alone or in combination with other methods, such as the administration of other active agents, e.g., therapeutic or prophylactic agents and/or immunosuppressive agents as are known in the art.

By "contacting" is meant administering the recombinant vector to the cell in such a manner and in such an amount as to effect physical contact between the vector and cell. If the viral vector is a recombinant viral particle, desirably, attachment to and infection of the cell by the viral vector is effected by such physical contact. If the viral vector is other than a recombinant viral particle, such as a nonencapsidated viral nucleic acid or other nucleic acid, desirably, infection of the cell by the nucleic acid is effected.

Such "contacting" can be done by any means known to those skilled in the art, and described herein, by which the apparent touching or mutual tangency of the vector with the cell can be effected. Optionally, the vector, such as an adenoviral vector, can be further complexed with a bispecific or multispecific molecule (e.g., an antibody or fragment thereof), in which case "contacting" involves the apparent touching or mutual tangency of the complex of the vector and the bispecific or multispecific molecule with the cell. For example, the vector and the bispecific (multispecific) molecule can be covalently joined, e.g., by chemical means known to those skilled in the art, or other means. Preferably, the vector and the bispecific (multispecific) molecule can be linked by means of noncovalent interactions (e.g., ionic bonds, hydrogen bonds, Van der Waals forces, and/or nonpolar interactions). Although the vector and the bispecific (multispecific) molecule can be brought into contact by mixing in a small volume of the same solution, the cell and the complex need not necessarily be brought into contact in a small volume, as, for instance, in cases where the complex is administered to a host (e.g., a human), and the complex travels by the bloodstream to the cell to which it binds selectively and into which it enters. The contacting of the vector with a bispecific (multispecific) molecule preferably is done before the cell is contacted with the complex of the adenovirus and the bispecific (multispecific) molecule.

By "transgene" is meant a gene, which can be expressed in a cell contacted with a vector comprising the transgene and the expression of which is desirably prophylactically or therapeutically beneficial to the cell or the tissue, organ, organ system, organism or cell culture of which the cell is a part. A therapeutic gene can be one that exerts its effect at the level of RNA or protein. For instance, a protein encoded by a therapeutic gene can be employed in the treatment of an inherited disease, e.g., the use of a cDNA encoding the cystic fibrosis transmembrane conductance regulator in the treatment of cystic fibrosis.

Moreover, the therapeutic gene can exert its effect at the level of RNA, for instance, by encoding an antisense message or ribozyme, a protein that affects splicing or 3' processing (e.g., polyadenylation), or a protein that affects the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation.

By "means of inhibiting an immune response to the recombinant vector" is meant a means with which a cell can be brought into contact that inhibits an immune response to the recombinant vector as described above for "inhibiting." Preferably, the means of inhibiting an immune response to the recombinant vector is a TNF receptor fusion protein, a Fas receptor fusion protein, an IFN receptor fusion protein, a dominant negative of an ICSBP, a gene encoding a TNF receptor fusion protein, a gene encoding a Fas receptor fusion protein, a gene encoding an IFN receptor fusion protein, or a gene encoding a dominant negative of an ICSBP. The TNF receptor fusion protein preferably comprises an extracellular domain of a TNF receptor, such as TNF receptor I (TNFI), and either of the α chain of CD8 or IgG (or a functional fragment thereof). The Fas receptor fusion protein preferably comprises an extracellular domain of a Fas receptor and either of the α chain of CD8 or IgG (or a functional fragment thereof). Preferably, the means of inhibiting an immune response is other than the combination of a TNF receptor fusion protein (or gene encoding same) and a Fas receptor fusion protein (or gene encoding same). Desirably, the fusion protein is a fusion of proteins/peptides derived from the same species as the cell contacted in accordance with the present inventive method. See, U.S. Pat. No. 5,447,851 with regard to TNF-IgG fusion proteins. The methods described therein can be adapted for construction of Fas-IgG fusion proteins. With regard to the IFN receptor protein, there are a variety of candidate proteins that can be used to block interferon function extracellularly, at the cell membrane or at the level of transcription. One approach is to create a dominant negative mutant of STAT-1 in a manner similar to the approaches used for STAT-3 (Fukada et al., *Immunity*, 5, 449–460 (1996); and Horvath et al., *J. Virol.*, 70, 647–650 (1996)). The mutants either lack the COOH-terminal or have critical tyrosines replaced. Another approach involves the creation of a dominant negative version of an endogenous gene, such as Interferon Consensus Sequence Binding Protein (ICSBP; Thornton et al., *J. Immunol.*, 157, 5145–5154 (1996)). ICSBP normally is expressed in erythroid lineage cells and, itself, can be controlled by IFN induction. The normal function of ICSBP is to suppress activation of IFN inducible genes. It contains separable DNA binding and repressor domains with the dominant negative of ICSBP consisting of the N-terminal 121aa encompassing the DNA binding domain (termed ICSBP DBD; Sharf et al., *J. Biol. Chem.*, 270, 13063–13069 (1995)). When overexpressed in a stable cell line the gene product inhibits both type I and type II IFN-stimulated gene expression (Thorton et al. (1996), supra).

Accordingly, the means of inhibiting an immune response can be in the form of a biologically acceptable proteinaceous composition (e.g., a TNF receptor fusion protein or a Fas receptor fusion protein) or a biologically acceptable composition comprising a gene, which encodes a means of inhibiting an immune response and which can be expressed in the cell. This means to express the gene in a cell is within the skill in the art. In this regard, the recombinant vector comprising a transgene can further comprise a gene encoding a means of inhibiting an immune response to the recombinant vector. If the means of inhibiting an immune response is a gene and the gene is contained in a vector that is separate from the recombinant vector that comprises and expresses the transgene or the composition is proteinaceous, the composition comprising the means of inhibiting an immune response can be brought into contact with the cell prior to, simultaneously with, or subsequent to contact of the cell with the recombinant vector comprising and expressing the transgene, as long as the timing of the contact effects inhibition of an immune response to the vectors brought into contact with the cell.

The recombinant vector comprising a transgene preferably is a viral vector. More preferably, the viral vector is selected from the group consisting of an adenoviral vector, an adeno-associated viral vector, a herpes viral vector and a retroviral vector. Most preferably, the viral vector is an adenoviral vector. Desirably, if the recombinant vector is a viral particle, in particular an adenoviral vector, the immunogenicity of the capsid, e.g., the hexon protein of an adenoviral capsid, is reduced in accordance with methods known in the art.

A cell can be present as a single entity, or can be part of a larger collection of cells. Such a "larger collection of cells" can comprise, for instance, a cell culture (either mixed or pure), a tissue (e.g., epithelial or other tissue), an organ (e.g., heart, lung, liver, gallbladder, urinary bladder, eye or other organ), an organ system (e.g., circulatory system, respiratory system, gastrointestinal system, urinary system, nervous system, integumentary system or other organ system), or an organism (e.g., a bird, mammal, particularly a human, or the like). Preferably, the organs/tissues/cells being targeted are of the circulatory system (e.g., including, but not limited to heart, blood vessels, and blood), respiratory system (e.g., nose, pharynx, larynx, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to, brain and spinal cord, and special sense organs, such as the eye) and integumentary system (e.g., skin). Even more preferably, the cells are selected from the group consisting of heart, blood vessel, lung, liver, gallbladder, urinary bladder, and eye cells.

In particular, a cell with which a recombinant vector, such as a viral vector, in particular an adenoviral vector, is contacted differs from another cell in that the contacted cell comprises a particular cell-surface binding site that can be targeted by the recombinant vector. By "particular cell-surface binding site" is meant any site (i.e., molecule or combination of molecules) present on the surface of a cell with which the vector, e.g., adenoviral vector, can interact in order to attach to the cell and, thereby, enter the cell. A particular cell-surface binding site, therefore, encompasses a cell-surface receptor and, preferably, is a protein (including a modified protein), a carbohydrate, a glycoprotein, a proteoglycan, a lipid, a mucin molecule or mucoprotein, and the like. Examples of potential cell-surface binding sites include, but are not limited to: heparin and chondroitin sulfate moieties found on glycosaminoglycans; sialic acid moieties found on mucins, glycoproteins, and gangliosides; major histocompatability complex I (MHC I) glycoproteins; common carbohydrate molecules found in membrane glycoproteins, including mannose, N-acetyl-galactosamine, N-acetyl-glucosamine, fucose, and galactose; glycoproteins, such as ICAM-1, VCAM, E-selectin, P-selectin, L-selectin, and integrin molecules; and tumor-specific antigens present on cancerous cells, such as, for instance, MUC-1 tumor-specific epitopes. However, targeting an adenovirus to a cell is not limited to any specific mechanism of cellular interaction (i.e., interaction with a given cell-surface binding site).

In the context of the present invention, any suitable recombinant vector can be used. A "vector" is a vehicle for gene transfer as that term is understood by those of skill in the art. The vectors according to the invention include, but are not limited to, plasmids, phages, and viruses. A vector according to the invention comprises additional sequences and mutations. In particular, a vector according to the invention further comprises a nucleic acid comprising a transgene and/or at least one gene, which encodes a means of inhibiting an immune response to a recombinant vector and which can comprise a wholly or partially synthetically made coding or other genic sequence or a genomic or complementary DNA (cDNA) sequence and can be provided in the form of either DNA or RNA.

Preferably, the vector is a viral vector, such as an adenoviral vector, an adeno-associated viral vector, a herpes vector or a retroviral vector, among others. Most preferably, the viral vector is an adenoviral vector. An adenoviral vector can be derived from any adenovirus. An "adenovirus" is any virus of the family Adenoviridae, and desirably is of the genus Mastadenovirus (e.g., mammalian adenoviruses) or Aviadenovirus (e.g., avian adenoviruses). The adenovirus is of any serotype. Adenoviral stocks that can be employed as a source of adenovirus can be amplified from the adenoviral serotypes 1 through 47, which are currently available from the American Type Culture Collection (ATCC, Rockville, Md.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22–30, 32, 33, 36–39, and 42–47), subgroup E (serotype 4), subgroup F (serotypes 40 and 41), or any other adenoviral serotype. Preferably, however, an adenovirus is of serotypes 2, 5 or 9. Desirably, an adenovirus comprises coat proteins (e.g., penton base, hexon, and/or fiber) of the same serotype. However, also preferably, one or more coat proteins can be chimeric, in the sense, for example, that all or a part of a given coat protein can be from another serotype.

Although the viral vector, which is preferably an adenoviral vector, can be replication-competent, preferably, the viral vector is replication-deficient or conditionally replication-deficient. For example, the viral vector which is preferably an adenoviral vector, comprises a genome with at least one modification that renders the virus replication-deficient. The modification to the viral genome includes, but is not limited to, deletion of a DNA segment, addition of a DNA segment, rearrangement of a DNA segment, replacement of a DNA segment, or introduction of a DNA lesion. A DNA segment can be as small as one nucleotide or as large as 36 kilobase pairs, i.e., the approximate size of the adenoviral genome, or 38 kilobase pairs, which is the maximum amount that can be packaged into an adenoviral virion. Preferred modifications to the viral, in particular adenoviral, genome include, in addition to a modification that renders the virus replication-deficient, the insertion of a transgene and, additionally and preferably, at least one gene encoding a means of inhibiting an immune response to the recombinant vector comprising a transgene. A virus, such as an adenovirus, also preferably can be a cointegrate, i.e., a ligation of viral, such as adenoviral, genomic sequences with other sequences, such as those of a plasmid, phage or other virus.

In terms of an adenoviral vector (particularly a replication-deficient adenoviral vector), such a vector can comprise either complete capsids (i.e., including a viral genome, such as an adenoviral genome) or empty capsids (i.e., in which a viral genome is lacking, or is degraded, e.g., by physical or chemical means). Preferably, the viral vector comprises complete capsids, i.e., as a means of carrying a transgene and, optionally, at least one gene encoding an inhibiting means. Alternatively, preferably, a transgene and at least one inhibiting gene, as defined above, is carried into a cell on the outside of the adenoviral capsid.

To the extent that it is preferable or desirable to target a virus, such as an adenovirus, to a particular cell, the virus can be employed essentially as an endosomolytic agent in the transfer into a cell of plasmid DNA, which contains a marker gene and is complexed and condensed with polylysine covalently linked to a cell-binding ligand, such as transferrin (Cotten et al., *PNAS* (*USA*), 89, 6094–6098 (1992); and Curiel et al., *PNAS* (*USA*), 88, 8850–8854 (1991)). It has been demonstrated that coupling of the transferrin-polylysine/DNA complex and adenovirus (e.g., by means of an adenovirus-directed antibody, with transglutaminase, or via a biotin/streptavidin bridge) substantially enhances gene transfer (Wagner et al., *PNAS* (*USA*), 89, 6099–6103 (1992)).

Alternatively, one or more viral coat proteins, such as the adenoviral fiber, can be modified, for example, either by incorporation of sequences for a ligand to a cell-surface receptor or sequences that allow binding to a bispecific antibody (i.e., a molecule with one end having specificity for the fiber, and the other end having specificity for a cell-surface receptor) (PCT international patent application no. WO 95/26412 (the '412 application) and Watkins et al., "Targeting Adenovirus-Mediated Gene Delivery with Recombinant Antibodies," Abst. No. 336). In both cases, the typical fiber/cell-surface receptor interactions are abrogated, and the virus, such as an adenovirus, is redirected to a new cell-surface receptor by means of its fiber.

Alternatively, a targeting element, which is capable of binding specifically to a selected cell type, can be coupled to a first molecule of a high affinity binding pair and administered to a host cell (PCT international patent application no. WO 95/31566). Then, a gene delivery vehicle coupled to a second molecule of the high affinity binding pair can be administered to the host cell, wherein the second molecule is capable of specifically binding to the first molecule, such that the gene delivery vehicle is targeted to the selected cell type.

Along the same lines, since methods (e.g., electroporation, transformation, conjugation of triparental mating, (co-)transfection, (co-) infection, membrane fusion, use of microprojectiles, incubation with calcium phospate- DNA precipitate, direct microinjection; etc.) are available for transferring viruses, plasmids, and phages in the form of their nucleic acid sequences (i.e., RNA or DNA), a vector similarly can comprise RNA or DNA, in the absence of any associated protein, such as capsid protein, and in the absence of any envelope lipid. Similarly, since liposomes effect cell entry by fusing with cell membranes, a vector can comprise liposomes, with constitutive nucleic acids encoding the coat protein. Such liposomes are commercially available, for instance, from Life Technologies, Bethesda, Md., and can be used according to the recommendation of the manufacturer. Moreover, a liposome can be used to effect gene delivery and liposomes having increased tranfer capacity and/or reduced toxicity in vivo can be used. The soluble chimeric coat protein (as produced using methods described herein) can be added to the liposomes either after the liposomes are prepared according to the manufacturer's instructions, or during the preparation of the liposomes.

The vectors according to the invention are not limited to those that can be employed in the method of the invention, but also include intermediary-type vectors (e.g., "transfer vectors") that can be employed in the construction of gene transfer vectors.

A transgene and/or a gene encoding a means of inhibiting an immune response can be moved to or from a viral vector from or into baculovirus or a suitable prokaryotic or eukaryotic expression vector for expression of mRNA and production of protein, and for evaluation of other biochemical characteristics.

Accordingly, the present invention also provides a recombinant vector comprising a gene encoding a TNF receptor fusion protein comprising the extracellular domain of a TNF receptor, preferably TNF receptor I, and the α chain of CD8. Such a vector can further comprise a transgene. Preferably, the recombinant vector is a viral vector. More preferably, the viral vector is selected from the group consisting of an adenoviral vector, an adeno-associated viral vector, a herpes viral vector and a retroviral vector. Most preferably, the viral vector is an adenoviral vector.

Also provided by the present invention is a recombinant vector comprising a gene encoding a Fas receptor fusion protein comprising the extracellular domain of the Fas receptor and either of the α chain of CD8 or an IgG (or a functional fragment thereof). Such a vector can further comprise a transgene. Preferably, the recombinant vector is a viral vector. More preferably, the viral vector is selected from the group consisting of an adenoviral vector, an adeno-associated viral vector, a herpes viral vector and a retroviral vector. Most preferably, the viral vector is an adenoviral vector.

The present invention further provides a recombinant vector comprising a gene encoding an IFN receptor fusion protein. Such a vector can further comprise a transgene. Preferably, the recombinant vector is a viral vector. More preferably, the viral vector is selected from the group consisting of an adenoviral vector, an adeno-associated viral vector, a herpes viral vector and a retroviral vector. Most preferably, the viral vector is an adenoviral vector.

Recombinant baculoviral and prokaryotic and eukaryotic plasmids and expression vectors comprising a transgene and/or a gene encoding a means of inhibiting an immune response are also provided by the present invention.

In terms of the production of vectors according to the invention (including recombinant adenoviral vectors and transfer vectors), such vectors can be constructed using standard molecular and genetic techniques, such as those known to those skilled in the art. Vectors comprising virions or viral particles (e.g., recombinant adenoviral vectors) can be produced using viral vectors in the appropriate cell lines. Similarly, particles comprising one or more chimeric coat proteins can be produced in standard cell lines, e.g., those currently used for adenoviral vectors. These resultant particles then can be targeted to specific cells, if desired.

Alterations of native amino acid sequences to produce variant proteins and peptides for targeting or expression as a transgene, for example, can be done by a variety of means known to those skilled in the art. A variant peptide is a peptide that is substantially homologous to a given peptide, but which has an amino acid sequence that differs from that peptide. The degree of homology (i.e., percent identity) can be determined, for instance, by comparing sequence information using a computer program optimized for such comparison (e.g., using the GAP computer program, version 6.0 or a higher version, described by Devereux et al. (*Nucleic Acids Res.*, 12, 387 (1984)), and freely available from the University of Wisconsin Genetics Computer Group (UWGCG)). The activity of the variant proteins and/or peptides can be assessed using other methods known to those skilled in the art.

In terms of amino acid residues that are not identical between the variant protein (peptide) and the reference protein (peptide), the variant proteins (peptides) preferably comprise conservative amino acid substitutions, i.e., such that a given amino acid is substituted by another amino acid of similar size, charge density, hydrophobicity/hydrophilicity, and/or configuration (e.g., Val for Phe). The variant site-specific mutations can be introduced by ligating into an expression vector a synthesized oligonucleotide comprising the modified site. Alternately, oligonucleotide-directed site-specific mutagenesis procedures can be used, such as those disclosed in Walder et al., *Gene*, 42, 133 (1986); Bauer et al., *Gene*, 37, 73 (1985); Craik, *Biotechniques*, January 1995, pp. 12–19; and U.S. Pat. Nos. 4,518,584 and 4,737,462.

Any appropriate expression vector (e.g., as described in Pouwels et al., *Cloning Vectors: A Laboratory Manual* (Elsevior, N.Y.: 1985)) and corresponding suitable host cell can be employed for production of a recombinant peptide or protein in a host cell. Expression hosts include, but are not limited to, bacterial species within the genera Escherichia, Bacillus, Pseudomonas, Salmonella, mammalian or insect host cell systems, including baculoviral systems (e.g., as described by Luckow et al., *Bio/Technology*, 6, 47 (1988)), and established cell lines, such as COS-7, C127, 3T3, CHO, HeLa, BHK, and the like. An especially preferred expression system for preparing chimeric proteins (peptides) according to the invention is the baculoviral expression system wherein *Trichoplusia ni*, Tn 5B1-4 insect cells, or other appropriate insect cells, are used to produce high levels of recombinant proteins. The ordinary skilled artisan is, of course, aware that the choice of expression host has ramifications for the type of peptide produced. For instance, the glycosylation of peptides produced in yeast or mammalian cells (e.g., COS-7 cells) will differ from that of peptides produced in bacterial cells, such as *Escherichia coli*.

Covalently-bound complexes can be prepared by linking a chemical moiety to a functional group on the side chain of an amino acid of a peptide or protein or at the N- or C-terminus of the peptide or protein. Such modifications can be particularly useful, for instance, in constructing a bispecific or a multispecific molecule comprising a ligand to a cell-surface receptor attached to an antibody. Further modifications will be apparent to those of ordinary skill in the art.

Viral attachment, entry and gene expression can be evaluated initially by using the adenoviral vector containing the insert of interest to generate a recombinant virus expressing the desired protein or RNA and a marker gene, such as β-galactosidase. β-galactosidase expression in cells infected with adenovirus containing the β-galactosidase gene (Ad-LacZ) can be detected as early as two hours after adding Ad-Gluc to cells. This procedure provides a quick and efficient analysis of cell entry of the recombinant virus and gene expression, and is implemented readily by an artisan of ordinary skill using conventional techniques.

A vector of the present invention has utility in vitro. Such a vector can be used as a research tool in the study of viral clearance and persistence and in a method of assessing the efficacy of means of circumventing an immune response. Similarly, a vector, preferably a viral vector, specifically an adenoviral vector, which comprises a transgene and/or at least one gene encoding a means of inhibiting an immune response, can be employed in vivo.

In particular, recombinant viruses, such as adenoviruses, of the present invention can be used to treat any one of a number of diseases by delivering to cells corrective DNA, e.g., DNA encoding a function that is either absent or impaired. Diseases that are candidates for such treatment include, for example, cancer, e.g., melanoma or glioma, cystic fibrosis, genetic disorders, and pathogenic infections, including HIV infection.

Other applications of the method and constituents of the present invention will be apparent to those skilled in the art.

One skilled in the art will appreciate that many suitable methods of administering a recombinant vector (particularly an adenoviral vector) and means of inhibiting an immune response of the present invention to an animal (see, for example, Rosenfeld et al., *Science,* 252, 431–434 (1991); Jaffe et al., *Clin. Res.,* 39(2), 302A (1991); Rosenfeld et al., *Clin. Res.,* 39(2), 311A (1991); Berkner, *BioTechniques,* 6, 616–629 (1988)) are available, and, although more than one route can be used for administration, a particular route can provide a more immediate and more effective reaction than another route. Pharmaceutically acceptable excipients for use in administering the recombinant vector and/or means of inhibiting an immune response also are well-known to those who are skilled in the art, and are readily available. The choice of excipient will be determined in part by the particular method used to administer the recombinant vector and for means of inhibiting an immune response. Accordingly, the present invention provides a composition comprising a recombinant vector encoding a means of inhibiting an immune response, alone or in further combination with a transgene, in a suitable carrier, and there is a wide variety of suitable formulations for use in the context of the present invention. In particular, the present invention provides a composition comprising a recombinant vector comprising a gene encoding a TNF receptor fusion protein comprising the extracellular domain of TNF receptor I and the α chain of CD8 and a carrier therefor. The recombinant vector can further comprise a transgene. The present invention also provides a composition comprising a recombinant vector comprising a gene encoding a Fas receptor fusion protein comprising the extracellular domain of the Fas receptor and either of the α chain of CD8 or an IgG (or a functional fragment thereof) and a carrier therefor. This recombinant vector also can further comprise a transgene. Also provided is a composition comprising a recombinant vector comprising ICSBP DBD and either of the α chain of CDB or an IgG (or a functional fragment thereof). Similarly, this recombinant vector can further comprise a transgene.

Such compositions can further comprise other active agents, such as therapeutic or prophylactic agents and/or immunosuppressive agents as are known in the art.

The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, emulsions, gels, and the like containing, in addition to the active ingredient, such excipients as are known in the art.

Aerosol formulations can be made for administration via inhalation. These aerosol formulations can be placed into pressurized acceptable propellants, such as dichlorodifluoromethane, propane, nitrogen, and the like. They also can be formulated as pharmaceuticals for non-pressurized preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, suppositories can be made with the use of a variety of bases, such as emulsifying bases or water-soluble bases.

Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the transgene of interest, source of vector and/or means of inhibiting an immune response, the composition employed, the method of administration, and the particular site and organism being treated. However, preferably, a dose corresponding to an effective amount of a vector (e.g., an adenoviral vector according to the invention) is employed. An "effective amount" is one that is sufficient to produce the desired effect in a host, which can be monitored using several end-points known to those skilled in the art. For instance, one desired effect is nucleic acid transfer to a host cell. Such transfer can be monitored by a variety of means, including, but not limited to, a therapeutic effect (e.g., alleviation of some symptom associated with the disease, condition, disorder or syndrome being treated), or by evidence of the transferred gene or coding sequence or its expression within the host (e.g., using the polymerase chain reaction, Northern or Southern hybridizations, or transcription assays to detect the nucleic acid in host cells, or using immunoblot analysis, antibody-mediated detection, or particularized assays to detect protein or polypeptide encoded by the transferred nucleic acid, or impacted in level or function due to such transfer). These methods described are by no means all-inclusive, and further methods to suit the specific application will be apparent to the ordinary skilled artisan. In this regard, it should be noted that the response of a host to the introduction of a vector, such as a viral vector, in particular an adenoviral vector, as well as a vector encoding a means of inhibiting an immune response, can vary depending on the dose of virus administered, the site of delivery, and the genetic makeup of the vector as well as the transgene and the means of inhibiting an immune response.

Generally, to ensure effective transfer of the vectors of the present invention, it is preferable that about 1 to about 5,000 copies of the vector according to the invention be employed per cell to be contacted, based on an approximate number of cells to be contacted in view of the given route of administration, and it is even more preferable that about 3 to about 300 pfu enter each cell. However, this is merely a general guideline, which by no means precludes use of a higher or lower amount, as might be warranted in a particular application, either in vitro or in vivo. Similarly, the amount of a means of inhibiting an immune response, if in the form of a composition comprising a protein, should be sufficient to inhibit an immune response to the recombinant vector comprising the transgene. For example, the actual dose and schedule can vary depending on whether the composition is administered in combination with other pharmaceutical compositions, or depending on interindividual differences in pharmacokinetics, drug disposition, and metabolism. Similarly, amounts can vary in in vitro applications, depending on the particular cell type targeted or the means by which the vector is transferred. One skilled in the art easily can make any necessary adjustments in accordance with the necessities of the particular situation.

EXAMPLES

The following examples serve to illustrate the present invention and are not intended to limit its scope in any way.

With respect to the following examples, C57BL/6 (H2b), C57BL/6-Fas$^{lpr}$ (B6/Lpr) Balb/c/J (H2) and C3H (H2k) mice were obtained from Jackson Laboratory, Bar Harbor, Me. The mutant strain, CBA/Lpr$^{cg}$ (CBA/K1Jms/Lpr$^{cg}$), and the wild-type strain, CBA/++ (CRA/K1Jms), have been described previously (Matsuzawa et al., *J. Exp. Med.*, 171, 519–531 (1990)). Homozygous C.B-17 SCID mice (provided by Dr. George Carlson, Great Falls, Mont.) were bred and maintained in a specific pathogen-free environment at the animal facilities at the Hospital for Special Surgery (New York, N.Y.). Mice deficient in TNF-α expression (TNF-α −/−) were created by replacement-type homologous recombination (Marino et al., *PNAS USA*, 94, 8093–8098 (1997)). Perforin knockout mice (perf −/−) were as previously described (Walsh et al., *PNAS USA*, 91, 10854–10858 (1994)).

Adenovirus of serotype 5 (Ad5) expressing chloramphenicol acetyl transferase (CAT), i.e., Ad5-CAT, from a first generation adenoviral vector was used in all studies (Kass-Eisler et al., *PNAS USA*, 90, 11498–11502 (1993))

Test samples were analyzed for normal distribution and then compared by either of the Student's t-test (normal distribution) or the Mann-Whitney rank sum test (nonparametric data). Multiple comparisons were performed by ANOVA with the Student-Newman-Keuls method for pairwise comparisons.

Example 1

This example demonstrates the relative effects of Fas, perforin and TNF-α on clearance of adenovirus from a host.

Mice (perf−/−, P2, B6/++, B6/Lpr, and SCID (control, since do not clear adenoviral vectors due to a lack of B- and T-cells)) were anesthetized with methoxyflurane and the skins of the anesthetized mice were incised to expose the jugular veins. The mice were then injected intrajugularly with $5 \times 10^9$ viral particles of Ad5-CAT diluted to 100 μl with phosphate-buffered saline (PBS; 137 mM NaCl, 2.7 mM KCl, 10 mM Na$_2$HPO$_4$, pH 7.4) using a 28 g ½ (0.36 mm×13 mm) needle affixed to a 0.5 cc insulin syringe. Following the injection, the incision was sutured. Mice were sacrificed on a given day as specified, the livers were removed and homogenized in 2 ml of PBS per gram wet weight of tissue, and the resultant homogenates were processed for CAT assays.

CAT assays were performed as previously described (Kass-Eisler et al. (1993), supra). Initially, 1–5% of the total tissue homogenate was assayed. When the values were out of range of the assay (generally greater than 60% acetylated chloramphenicol), lysates were diluted in PBS containing 1 mg of bovine serum albumin (BSA) per ml. Each assay point included 5 animals from a single experiment.

Administration of $5 \times 10^9$ particles of Ad5-CAT by intrajugular injection produced uniformly high levels of CAT gene expression in all strains of mice that were examined seven days post-infection. Twenty-eight days post-infection, SCID mice continued to have persistently high elevations of CAT expression, whereas normal immunocompetent mice, namely P2 and B6/++, had baseline levels of CAT expression. The results observed for SCID mice were consistent with previous reports (Kass-Eisler et al. (1994), supra; Kass-Eisler et al. (1993), supra; and Kass-Eisler et al., *Gene Ther.*, 3, 154–162 (1996)). Surprisingly, the levels of CAT gene-expression were also reduced to baseline in perforin-deficient mice (perf −/−) at 28 days post-infection. The results observed for perforin-deficient mice indicated that perforin was not required for elimination of transgene expression. Fas-deficient Lpr mice showed a low level of persistent CAT gene expression at 28 days post-infection in comparison to the corresponding wild-type control. The results observed for Fas-deficient Lpr mice indicated that the Fas pathway contributes somewhat to host clearance of Ad5-CAT. TNF-α-deficient (TNF-α −/−) mice showed high levels of CAT expression at 24 days post-infection in comparison to the corresponding wild-type control (TNF-α +/+). At 60 days post-infection, however, TNF-α-deficient mice were able to inhibit transgene expression completely. These results in TNF-α-deficient mice indicate that other host defense mechanisms eliminate transgene expression over a prolonged period of time. These finding are clearly not explained by differences between strains of mice inasmuch as similar results were observed in CBA Lpr$^{cg}$ mice that have a point mutation in the signal transducing region of the Fas receptor (Watanabe-Fukunaga et al., *Nature*, 356, 314–317 (1992)).

Example 2

This example demonstrates the cytolysis of adenovirus-infected fibroblasts by TNF-α-deficient cytotoxic T-cells.

The spleens from Ad5-CAT-infected mice were aseptically removed and single cell suspensions were prepared. Spleen cells were cultured at a density of $4 \times 10^6$ cells/ml (1.5 ml per well of 24-well plates) in α-MEM with supplements as above in the presence of Ad5-CAT at a multiplicity of infection (moi) of 50. After five days in culture, reactivated cytotoxic T-cells were harvested, washed and resuspended at desired concentrations in culture medium.

Embryonic fibroblasts were infected with Ad5-CAT at a moi of 500 for 24 hr prior to use as target cells. Infected fibroblasts, as well as uninfected control fibroblasts, were detached from the culture plates and labeled with $^{51}Cr$ (~100 $\mu Ci/10^6$ cells) for 1.5 hr in suspension.

Cytotoxic T-cells and labeled target cells ($10^4$ cells/well), at different effector:target ratios, were added to individual wells of round-bottomed 96-well microtiter plates and incubated at 37° C. for 5 hrs. The percentage of target cell lysis induced by cytotoxic T-cells was determined by quantifying $^{51}Cr$ released from target cells, based on the following equation:

% specific release (cytolysis)=(experimental release−spontaneous release)×100%. (total release−spontaneous release)

Significant lysis of virus-infected fibroblasts and, to a lesser extent, of uninfected fibroblasts was detected in assays employing cytotoxic T-cells derived from wild-type, Lpr, and TNF-α −/−mice at 28 days post-infection with Ad5-CAT. In contrast, only marginal lysis of virus-infected fibroblasts was detected in assays employing cytotoxic T-cells derived from perf−/− mice.

Reactivated cytotoxic T-cells prepared from all strains of mice induced substantial lysis of YAC-1 cells, which are the classical NK target cells. Lysis of YAC-1 cells by reactivated cytotoxic T-cells prepared from all strains of mice indicates that NK cells and lymphokine-activated killer (LAK) cells are present in the bulk population of reactivated cells. The presence of NK and LAK cells provides an explanation for the low degree of killing of uninfected fibroblasts observed in the cytotoxic T-cell cytotoxicity assays. Given that the subclone of YAC-1 cells used expresses a substantial level of Fas antigen, the lysis of YAC-1 cells by perforin −/− lymphocytes was most likely mediated by the Fas-dependent pathway.

Example 3

This example demonstrates that TNF-α mediates clearance of adenovirus-mediated transgene expression in vitro and in vivo by inducing cytolysis.

Twelve SCID mice were infected with Ad5-CAT. Seven and 14 days post-infection, half the mice received either 80,000 units of recombinant mouse TNF-α or saline by intraperitoneal injection. The mice were sacrificed at 21 days post-infection and CAT gene expression in the liver was measured. All animals that received intraperitoneal injections of TNF-α had levels of CAT expression identical to those found in the control group. These findings indicated that systemic TNF-α did not mediate clearance of adenovirus from Ad5-CAT-infected hepatocytes in vivo.

A fibroblast assay was established to determine whether or not TNF-α mediated noncytolytic clearance of adenovirus from Ad5-CAT-infected cells in vitro. Murine embryonic fibroblasts were prepared from embryos of the C57Bl/6 ($H2^b$) strain at the fetal age of 16 days, following a standard procedure (Doetschman et al., *J. Embryol. Exp. Morphol.*, 87, 27–45 (1985)) with minor modifications. Briefly, embryos were aseptically removed, rinsed with PBS, cut into small pieces, and incubated at 4° C. in PBS containing 0.05% trypsin and 1 mM EDTA (PBS/trypsin/EDTA) overnight. Following the removal of particulate debris, embryonic cells released into the medium were plated onto 100 mm plates and cultured in α-modified minimum essential medium (αMEM) supplemented with 5% fetal bovine serum (FBS, Hyclone Laboratories, Inc., Logan, Utah), penicillin/streptomycin (5,000 U/50 μg/ml), and $5 \times 10^{-5}$ M 2-mercaptoethanol at 37° C. Embryonic fibroblasts were harvested by trypsinization, washed, and either split for continuing culture or frozen as stocks. Fibroblasts of the third passage were used in most experiments.

$H$-$2^b$ fibroblasts were infected with Ad5-CAT at 1,000 particles/cell. Twenty-four hours post-infection, cells were labeled with $^{51}Cr$ and exposed to increasing concentrations of TNF. Cell lysis was assessed at 2 hrs, 4 hrs, 10 hrs and 18 hrs by $^{51}Cr$ release and CAT transgene expression was quantified as described above. A decline in CAT activity was observed to correlate directly with the degree of cell lysis, indicating that TNF-α exerts its effect by inducing cell lysis.

Example 4

This example demonstrates reduced lymphocytic infiltration of the liver of TNF-α wild-type (+/+) mice as compared to TNF-α -deficient (−/−) mice.

TNF-α −/− and TNF-α +/+ mice were infected with Ad5-CAT and sacrificed at 7 days post-infection. Livers were removed from the mice, fixed in formalin, embedded in paraffin, and sectioned. Sections of the livers were stained with hematoxylin and eosin. Wild-type mice showed extensive lymphocytic infiltration of the liver, averaging 8.6±2.3 inflammatory foci per low power field. In contrast, TNF-α-deficient mice showed a significant reduction in lymphocytic infiltrates (i.e., mononuclear cell clusters, 1.6±1.5 foci per field, $p<0.0005$, n=5, Student's t-test).

These results are consistent with earlier studies, which demonstrated that adenoviral vector infection leads to $CD4^+$ and $CD8^+$ lymphocyte infiltration of the liver, which peaks around 7–10 days post-infection (Yang et al. (1994a), supra). The results are also consistent with TNF-α acting as a potent stimulator of adhesion molecules, which, in turn, facilitates leukocyte adhesion to vessels and transendothelial migration (Springer, *Nature*, 346, 425–434 (1990)).

Example 5

This example describes the titers of neutralizing antibodies to adenovirus.

Given that it has been recently observed that TNF-α −/− mice have an impaired antibody production (Marino et al. (1997), supra; and Pasparakis et al., *J. Exp. Med.*, 184, 139–411 (1996)), the titers of IgG anti-adenoviral antibodies to Ad5-CAT were quantified in TNF-α +/+ and −/− mice. The titers of neutralizing antibodies to Ad5-CAT was determined for 28 d.p.i. serum as described in Gall et al. (*J. Virol.*, 70, 2116–2123 (1996)). Anti-Ad antibodies were measured by ELISA in 96-well plates coated with $10^{10}$ particles (approx. 50 ng) per well of adenovirus in PBS at 4° C. overnight. The wells were washed and then blocked with 1% BSA at room temperature for 1 hr. The plates were then serially incubated with mouse sera (1/1,000 dilution in 3% BSA, 10% normal goat serum, 0.05% Tween-20, PBS), a 1/1,000 dilution of alkaline phosphatase-conjugated goat anti-mouse IgG and developed with substrate (Sigma 104 phosphatase substrate, Sigma Chemical Co., St. Louis, Mo.). Plates were read at 405 nm in an ELISA reader. Analysis of serum from Ad5-CAT-infected TNF-α-deficient mice showed significantly reduced anti-Ad5 antibody compared to Ad5-CAT-infected wild-type mice. The low titer of anti-Ad5-CAT antibody in the TNF-α-deficient mice was confirmed by the lack of serum neutralization activity in in vitro anti-Ad5 serum neutralization assays.

Example 6

This example describes the construction of a fusion protein comprising the extracellular domain of either of the TNF receptor I (TNFRI) or the Fas receptor (FasR) and the extracellular domain of the α-chain of CD8.

Total RNA was extracted from lung tissue by RNAzol (Tel Test, Friendswood, Tex.) according to the manufacturer's protocol. cDNAs were synthesized with the Superscript Kit (Gibco, Gaithersburg, Md.). PCR amplification (30 cycles) was performed with primers specific for CD8 (5') paired with either TNFRI or Fas (3'). RT-PCR for β-actin was used as a housekeeping gene control. CAT cDNA was amplified using PCR (40 cycles). PCR with common primers was used to amplify the adenoviral (Ad) vector spanning the different transgenes.

The extracellular domains of murine TNFRI, FasR and the α chain of CD8 were amplified from cDNA using PCR. Chimeric TNFRICD8 and FasRCD8 fusion proteins were created by overlapping PCR, taking care to avoid the introduction of foreign amino acids.

All fragments were ligated between the Hin dIII and Xho I site of pAd. The viruses expressing TNFRICD8 and FasRCD8 were produced by co-transfecting a pAd vector containing a transgene with PJM17 into 293 cells. The cell lysate was used to infect 293 cells. Viral DNA was extracted by a modified Hirt assay and recombination was verified by restriction enzyme digestion and PCR and the protein product was verified by ELISA. The viruses were futher plaque purified. Each clone was rescreened as above. Finally, large scale virus was purified by two-step CsCl concentration and stored in glycerol at −20° C. or sucrose at −70° C. Quantitation of viral particles was measured at OD 260 nm.

In order to determine whether full-length, functional proteins were produced, HeLa cells were transiently infected with the Ad vectors and the culture medium was tested for protein expression by ELISA and Western blot analysis. Anti-CD8-α chain, TIB 105 hybridoma (ATCC, Rockville, Md.), mouse YST 169 (Caltag, Duckinggame, Calif.), anti-Fas, Jo-2 (Pharmingen, San Diego, Calif.), R-anti-Fas, a rabbit polyclonal antibody (Drappa et al., *PNAS USA*, 90, 10340–10344 (1993)), and anti-TNFR1 (Genzyme, Cambridge, Mass.) antibodies were used.

ELISA plates were coated with antibody (5 μg/ml) overnight at 4° C. The plates were blocked with PBS/3% BSA for 1 hr at room temperature and then incubated with the test sample for 4–5 hrs at room temperature. The plates were washed and sequentially incubated with biotinylated secondary antibody, avidin-alkaline phosphatase and substrate. The O.D. was read at 405 nm. Unless indicated otherwise, samples were tested at the following dilutions: cell culture supernates, neat; serum, ½; bronchio-alveolar lavages (BALs), neat. To obtain a standard for ELISA, FasCD8 was isolated from culture supernatants by step elution on a DEAE ion exchange column. The protein was isolated to ~70% purity as determined by silver staining and Western blot analysis.

All three proteins could be detected by ELISA using two different monoclonal antibodies (mAb) to CD8. These results were specific, since, when the coating Ab was directed against either FasR or TNFRI, only the appropriate transgene product was detected.

SDS polyacrylamide gel electrophoresis (PAGE) was performed on a 12% gel under reducing conditions. Western blotting was performed as described (Bullard et al., *J. Immunology*, 159, 2058–2067 (1997)) using the rabbit anti-FasR or goat anti-TNFR antibodies mentioned above. In order to evaluate the molecular mass of the fusion proteins under non-denaturing conditions, gel filtration on a Sephadex-G100 column (Pharmacia, Piscataway, N.J.) equilibrated in phosphate-buffered saline (PBS) was performed following calibration with IgG, BSA and ovalbumin (OVA). Concentrated supernate from virus-infected 293 cells was loaded onto the column and 1 ml fractions were collected. FasRCD8 or TNFRCD8 was detected by ELISA as above. The same supernates were run on the same column under dissociating conditions (0.2% SDS).

Western blot analysis revealed that TNFRCD8 and FasCD8 had M.W. of ~60 and 56 kD repectively, consistent with the sizes predicted from the DNA sequences and glycoslation (Watanabe-Fukunaga et al., Nature, *356*, 314–317 (1992)). In order to examine the molecular weight of these fusion proteins under native (PBS) and dissociating (0.5% SDS) conditions, culture supernates were applied to a Sephadex G100 gel filtration column and the fusion proteins were detected by ELISA. Under native conditions, TNFRCD8 and FasRCD8 eluted near the void volume of the column, whereas under dissociating conditions, the size of TNFRCD8 was ~45 kD.

Example 7

This example demonstrates that the CD8 fusion proteins specifically inhibit their cognate ligands in vitro.

In order to ensure that the fusion proteins retained the function of binding authentic ligand, the culture supernates containing each protein were tested in an in vitro functional assay.

In order to evaluate FasRCD8 function, FasRCD8 or CD8 supernatants were incubated with soluble functional human Fas ligand (FasL; Orlinick et al., *J. Biol. Chem.*, 272, 32221–32229 (1997)) at 4° C. for 6 hrs. The supernatants were then incubated with the FasL-sensitive cell line A20 (Onel et al., *Eur. J. Immunol.*, 25, 2940–2947 (1995)), and apoptosis was quantified by the alamar blue assay of viability (Onel et al. (1995), supra) 12–16 hrs later. FasCD8 attenuated FasL mediated apoptosis of the B cell lymphoma A20.

In order to evaluate TNFRICD8 function, recombinant TNF-α (Genzyme) was incubated with TNFRICD8 or FasRCD8 supernatants at 4° C. for 6 hrs. Cytotoxicity was then evaluated at 16 hrs by the alamar blue assay using the L929 cell line in the presence of cycloheximide (10 μg/ml). TNFRCD8 efficiently inhibited TNF-α induced death of L929 cells.

Since CD8 can bind to MHC I via its CDR1 and CDR2 domains, the possible interference of soluble CD8 was also evaluated in a classical allogenic CTL reaction. Allogenic CTL reactions were generated by injecting C3H B6/F1 spleen cells into C3H mice. Spleen cells were harvested at 7 days and tested for cytotoxicity against $^{51}$Cr labeled EL4 cell ($H2^b$) targets. The percent lysis was calculated according to the formula: [(cpm sample−cpm spontaneous)/(cpm maximum−cpm spontaneous)]×100%. Addition of supernates containing FasRCD8 or TNFRICD8 failed to inhibit this in vitro reaction. In addition, no evidence for binding of these fusion proteins to several MHC I positive cell lines (AE7, EL4) was observed by flow cytometry analysis.

Example 8

This example demonstrates that the soluble Fas and TNF fusion proteins are expressed and functional in vivo.

Purified viruses were injected into BALB/c mice intravenously and serum was assayed for transgene expression at 1 week post injection. The level of expression of the transgene product in mouse serum was comparable to the in vitro supernates.

In order to determine whether the secreted soluble fusion proteins were functional, inducers of cell death were administered to Ad-infected SCID mice at 1 week post-infection. Hepatic apoptosis was induced through the Fas receptor (Ogasawara et al., Nature, 364, 806–809 (1993)) by intravenous injection of SCID mice with 6 μg of the anti-Fas antibody Jo-2. The mice were observed for 24 hr and any live mice were sacrificed. The 6 μg of Jo2 induced massive hepatic apoptosis in SCID mice infected with the control AdCAT virus (all 3 mice died by 24 hr), whereas mice infected with AdFasRCD8 were substantially protected (none of the mice died at 24 hr, at which time they were sacrificed).

In order to investigate the functional capacity of TNFRICD8 fusion protein in vivo, the high sensitivity of mice to lethal shock when exposed to bacterial LPS systemically was exploited. TNF-α mediated septic shock was induced by sensitizing C3HeSnJ mice and then injecting the mice with LPS as described (Marino et al., (1997), supra). Briefly, three C3H/HeSnJ mice per group were injected with $2.4 \times 10^8$ pfu of AdTNFRICD8 or AdCAT control. Five days later, they were sensitized with 25 mg D-galactosamine (D-gal) followed by 0.3 μg LPS intraperitoneally. The mice were observed for 3 days, after which surviving mice were sacrificed. At the time of death, the livers were harvested and snap-frozen in liquid nitrogen or fixed in formalin. Formalin-fixed tissue was embedded in paraffin and sections were stained with hematoxylin and eosin for examination by light microscopy. All of the three mice injected with AdCAT died within 6 hrs of injection of LPS. In striking contrast, all of the three mice that had been injected with AdTNFRICD8 survived. At autopsy (immediately after death), the AdCAT injected mice showed extensive hemorrhagic liquification of the liver, whereas mice receiving AdTNFRICD8 were protected.

Example 9

This example demonstrates the duration of transgene expression in the liver.

Since it is assumed that SCID mice infected with the Ad vectors expressing CD8, TNFRICD8 or FasRCD8 would produce comparable levels of soluble product in serum, the sensitivity of the ELISAs for the different proteins in SCID serum was compared. The sensitivities of the capture ELISAs were several-fold higher for FasRCD8 and TNFRICD8 compared to CD8 alone. Further studies were, therefore, performed with AdFasRCD8 and AdTNFRICD8 only. In order to determine whether inhibition of Fas or TNF-α prolonged expression of the respective fusion proteins in normal mice, mice were infected intravenously and tested for fusion protein expression by ELISA. Serum levels of FasCD8 peaked at week 1 and then approached background levels after 2 weeks. When compared to a partially purified standard, the concentration of fusion protein in serum was estimated at ~4 μg/ml. In the case of TNFRICD8, serum levels were sustained until week 2 and declined in the third week. In order to examine the effect of co-injection of AdFasRCD8 and AdTNFRICD8, both vectors were injected intravenously and the level of FasRCD8 was monitored in the serum. Co-expression of both fusion proteins resulted in persistence of FasRCD8 so that the levels approximated TNFRICD8.

Example 10

This example demonstrates that the absence or lockade of TNFα prolongs transgene expression in the lung.

In order to determine whether the immune response in the airway was similar to that in the liver, AdCAT was administered to TNF-α-deficient mice and Fas-deficient mice by the intratracheal route and CAT expression in the lungs was quantified. At 4 weeks post-injection, CAT activity was significantly higher in lung tissue obtained from TNF-α-deficient mice but not Fas-deficient mice compared to wild-type mice. Whether or not the soluble fusion proteins would promote virus persistence in the lung was also examined. When B6 mice were infected with AdTNFRICD8, AdFasRCD8 or AdCD8 by the intratracheal route, relatively high levels (compared to the SCID control) of TNFRICD8, but not FasRCD8 or CD8 proteins, were detected in BALs 4 weeks post-administration. In view of the differences in sensitivities of the EL ISAs, mRNA transcription of the transgenes was evaluated with the same primer pairs used to create the transgene. RT-PCR confirmed continued transcription of the TNFRICD8 trangene mRNA in 4 out of 5 mice and FasRCD8 in 0/4 mice, whereas CD8 mRNA was barely detectable in all of the five mice. Similar results were obtained when common vector primers were used for PCR. These findings indicate that blockade of TNF-α in the lung has a similar protective effect on immune elimination as observed in the liver but that Fas plays a lesser role in the lung than that previously observed in the liver.

Example 11

This example demonstrates that TNFRICD8 transprotects for a second gene product.

AdTNFRICD8 and AdCAT were co-injected intravenously and CAT expression was evaluated at day 21. Co-expression of AdTNFRICD8 with AdCAT markedly enhanced CAT expression at 21 days compared to AdCAT alone. In order to determine whether this effect could also be seen in the lung, the three transgenes were co-administered with AdCAT intratracheally and expression of CAT was quantified at day 28. TNFRICD8 offered significantly greater protection for CAT expression compared to the other transgenes. When analyzed at the level of transcription, CAT mRNA was only detected in AdTNFRICD8-infected lungs. CAT mRNA expression was not detected in the lungs of mice infected with AdCAT alone. Together, these findings indicate that TNFRICD8 can extend expression of a foreign transgene product and that this expression is due to continued transcription.

Example 12

This example demonstrates that TNFRICD8 attenuates the humoral immune response to adenovirus.

The effect of TNF-α blockade on humoral responses to Ad in the liver and lung 4 weeks post-infection was examined. Quantitation of anti-adenovirus IgG was performed essentially as described in Example 5. Briefly, plates were coated with purified adenovirus ($10^8$ particle/well) at 4° C. overnight. Following blocking with 3% BSA, serum samples were diluted from 1/10 to 1/2000 and incubated with antigen. The plates were sequentially blocked with 3% BSA, incubated with serum (diluted 1/2,000 for intravenously and 1/200 for intratracheally infected mice) and alkaline phosphatase conjugated anti-mouse IgG. Following intravenous administration, IgG responses in AdTNFRICD8 mice were substantially reduced compared to controls. In contrast, mice infected with AdFasCD8 alone or both vectors simultaneously had similar antibody responses to controls. When mice were infected with AdTNFRICD8 by the intratracheal route, there was a statistically significant reduction in anti-Ad antibodies compared to controls 4 weeks post-infection. These findings demonstrate that inhibition of TNF-α action in the liver and the lung markedly diminish IgG anti-Ad antibody production in normal mice.

Example 13

This example describes the construction of a bifunctional adenoviral vector expressing CD8 (reporter gene) and ICSBP-DBD.

ICSBP-DBD was inserted into the Hind III/Sal I sites of the standard expression cassette pAdSCMV-HSgD and in the expression cassette pAdTCMV-CD8. Each expression cassette is initially characterized by transfection into 293 cells and isolation of nuclear lysates. Gel mobility shift assays and immune precipitation assays of transfected extracts are used to characterize ICSBP-DBP functionally. Once a positive demonstration of ICSBP-DBD has been accomplished, viral vectors are constructed using a standard E3-deleted viral backbone.

Example 14

This example describes the in vitro characterization of Ad5CMV-ICSBP-DBD.

Infection with Ad5CMV-ICSBP-DBD is initially characterized in vitro by the time course of ICSBP-DBD expression following virus infection under increasing dose of virus, gel mobility shifts of nuclear extracts following time course and dose response, and isolation of RNA in a time course following infection with Ad-sCD8 versus Ad5-CMV-ICSBP DP/sCD8. Once expression is confirmed, RNAse protection assays are used to characterize the influence of expression of ICSBP-DBD on interferon inducible genes, which are activated in response to virus infection (ISG-15/54). Then, dual vectors with expression of soluble TNFRCD8 or with E3 are generated and tested for synergistic suppression of TNF-α and IFN. Alternatively, co-infection can be used.

All patents, patent applications, journal articles and other references cited herein are hereby incorporated by reference to the same extent as if each reference were individually and specifically indicated to be incorporated by reference and were set forth in its entirety herein.

While this invention has been described with emphasis upon preferred embodiments, it will be obvious to those of ordinary skill in the art that the preferred embodiments can be varied. It is intended that the invention may be practiced otherwise than as specifically described herein. Accordingly, this invention includes all modifications encompassed within the spirit and scope of the appended claims.

What is claimed is:

1. A method of inhibiting an antibody response to a recombinant adenoviral vector, which method comprises contacting a cell in vivo with (i) a recombinant adenoviral vector comprising a transgene and (ii) a recombinant adenoviral vector encoding a TNF receptor fusion protein comprising the extracellular domain of the TNF receptor I and the extracellular domain of the CD8α chain, whereupon an antibody response to the recombinant adenoviral vector comprising the transgene is inhibited.

2. The method of claim 1, wherein said recombinant adenoviral vector comprising the transgene and said recombinant adenoviral vector encoding the TNF receptor fusion protein are the same vector.

3. A recombinant adenoviral vector comprising a gene encoding a TNF receptor fusion protein comprising the extracellular domain of TNF receptor I and the α chain of CD8.

4. The recombinant adenoviral vector of claim 3, which further comprises a transgene.

5. A composition comprising the recombinant adenoviral vector of claim 3 and a carrier therefor.

6. A composition comprising the recombinant adenoviral vector of claim 4 and a carrier therefor.

* * * * *